United States Patent
Moszner et al.

(10) Patent No.: US 9,320,686 B2
(45) Date of Patent: *Apr. 26, 2016

(54) DENTAL MATERIALS BASED ON COMPOUNDS HAVING DEBONDING-ON-DEMAND PROPERTIES

(75) Inventors: Norbert Moszner, Mauren (LI); Thomas Hirt, Rebstein (CH); Kai Rist, Feldkirch (AT); Ulrich Salz, Lindau (DE); Christoph Weder, Düdingen (CH); Gina Fiore, Marly (CH); Christian Heinzmann, Fribourg (CH); Volker Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 57 days.

This patent is subject to a terminal disclaimer.

(21) Appl. No.: 14/343,300

(22) PCT Filed: Sep. 10, 2012

(86) PCT No.: PCT/EP2012/067680
§ 371 (c)(1),
(2), (4) Date: Jun. 20, 2014

(87) PCT Pub. No.: WO2013/034778
PCT Pub. Date: Mar. 14, 2013

(65) Prior Publication Data
US 2014/0371341 A1  Dec. 18, 2014

(30) Foreign Application Priority Data

Sep. 8, 2011 (EP) .................................. 11180645

(51) Int. Cl.
| | | |
|---|---|---|
| A61K 6/083 | (2006.01) |
| A61C 7/00 | (2006.01) |
| A61K 6/00 | (2006.01) |
| C07D 239/47 | (2006.01) |
| C07F 3/06 | (2006.01) |
| C08F 122/22 | (2006.01) |

(52) U.S. Cl.
CPC ............. A61K 6/0835 (2013.01); A61K 6/0002 (2013.01); A61K 6/0023 (2013.01); A61K 6/083 (2013.01); C07D 239/47 (2013.01); C07F 3/06 (2013.01); C08F 122/22 (2013.01)

(58) Field of Classification Search
CPC ...... C09J 133/14; A61K 6/083; C08F 120/02; C08F 128/02; C08F 130/02
USPC ........................................ 523/116; 433/228.1
See application file for complete search history.

(56) References Cited

U.S. PATENT DOCUMENTS

| | | | |
|---|---|---|---|
| 6,764,569 B1 | 7/2004 | Becher et al. | |
| 7,919,110 B2 * | 4/2011 | Richard | ........................ 424/425 |
| 7,935,131 B2 | 5/2011 | Anthamatten et al. | |
| 2006/0165753 A1 | 7/2006 | Richard | |
| 2007/0142494 A1 | 6/2007 | Kalgutkar et al. | |
| 2007/0142497 A1 | 6/2007 | Kalgutkar et al. | |

(Continued)

FOREIGN PATENT DOCUMENTS

| | | |
|---|---|---|
| DE | 19832629 A1 | 2/2000 |
| WO | 02/46260 A1 | 6/2002 |

(Continued)

OTHER PUBLICATIONS

Braun, D., et al., Synthese und Zerfall von Azionitiatoren, I., Monatshefte für Chemie, 1982, vol. 113, pp. 1403-1414.

(Continued)

*Primary Examiner* — Tae H Yoon
(74) *Attorney, Agent, or Firm* — Ann M. Knab; Thad McMurray (57) ABSTRACT

The invention relates to a dental restorative material which comprises a thermolabile compound of Formula I:

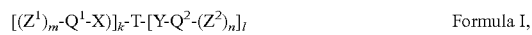

$$[(Z^1)_m\text{-}Q^1\text{-}X]_k\text{-}T\text{-}[Y\text{-}Q^2\text{-}(Z^2)_n]_l \qquad \text{Formula I,}$$

in which T represents a thermolabile unit which contains at least one thermolabile group based on non-covalent interactions, $Z^1$ and $Z^2$ in each case independently represent a polymerizable group selected from vinyl groups, $CH_2=CR^1-CO-O-$ and $CH_2=CR^1-CO-NR^2-$ or an adhesive group selected from $-Si(OR)_3$, $-COOH$, $-O-PO(OH)_2$, $-PO(OH)_2$, $-SO_2OH$ and $-SH$, $Q^1$ in each case independently is missing or represents an (m+1)-valent linear or branched aliphatic $C_1$-$C_{20}$ radical which can be interrupted by $-O-$, $-S-$, $-CO-O-$, $-O-CO-$, $-CO-NR^3-$, $-NR^3-CO-$, $-O-CO-NR^3-$, $-NR^3-CO-O-$ or $-NR^3-CO-NR^3-$, $Q^2$ in each case independently is missing or represents an (n+1)-valent linear or branched aliphatic $C_1$-$C_{20}$ radical which can be interrupted by $-O-$, $-S-$, $-CO-O-$, $-O-CO-$, $-CO-NR^3-$, $-NR^3-CO-$, $-O-CO-NR^3-$, $-NR^3-CO-O-$ or $-NR^3-CO-NR^3-$, X and Y in each case independently are missing or represent $-O-$, $-S-$, $-CO-O-$, $-O-CO-$, $-CO-NR^3-$ or $-NR^3-CO-$, R, $R^1$, $R^2$ and $R^3$ in each case independently represent H or a $C_1$-$C_7$ alkyl radical, k and l in each case independently are 0, 1, 2 or 3 and m and n in each case independently are 1, 2 or 3.

26 Claims, 2 Drawing Sheets

(56) References Cited

U.S. PATENT DOCUMENTS

| | | |
|---|---|---|
| 2007/0142498 A1 | 6/2007 | Brennan et al. |
| 2012/0114952 A1 | 5/2012 | Bauer et al. |

FOREIGN PATENT DOCUMENTS

| | | |
|---|---|---|
| WO | 2008/005173 A1 | 1/2008 |
| WO | 2010/002262 A1 | 1/2010 |
| WO | 2010/128042 A1 | 11/2010 |

OTHER PUBLICATIONS

McKillip, W.J., et al., Furan and Derivatives, Ullmann's Encyclopedia of Industrial Chemistry, 5th Ed., vol. A 12, Formamides to Hexamthylenediamine, VCH, Weinheim etc., 1989, pp. 119-134.

Folmer, B.J.B., et al., Supramolecular Polymer Materials: Chain Extension of Telechelic Polymers Using a Reactive Hydrogen-Bonding Synthon, Adv. Mater., 2000, vol. 12, No. 12, pp. 874-878.

Becker, H.G.O., et al., Chapter 4.4.4 [4+2]-Cycloadditionene (Diels-Alder-Reaktion), Organikum, Organisch-chemisches Grundpraktikum, Wiley-VCH, 2001, vol. 21, Weinheim pp. 330-333.

Quinn, S., Chemical blowing agents: providing production, economic and physical improvements to a wide range of polymers, Plastics, Additives & Compounding, May 2001, vol. 3, pp. 16-21.

Walter, W., et al., Chapter 7.1.3.3 Paal-Knorr-Synthese, Beyer-Walter, Lehrbuch der Organischen Chemie, S. Hirzel Verlag, Stuttgart und Liepsiz, 2004, vol. 24, p. 769.

Rowan, S.J., et al., Metal-ligand induced supramolecular polymerization: A route to responsive materials, Faraday Discussions, 219 Aug. 2004, vol. 128, pp. 43-53.

Sivakova, S., et al., Nucleobases as supramolecular motifs, Chem. Soc. Rev., Dec. 6, 2004, vol. 34, pp. 9-21.

De Greef, T.F.A., et al., Supramolecular polymers, Nature, May 8, 2008, vol. 453, pp. 171-173.

Fox, J.D., et al., Supramolecular Polymerizations and Main-Chain Supramolecular Polyers, Macromolecules, 2009, vol. 42, pp. 6823-6835.

Burattini, S., et al., A Healable Supremolecular Polymer Blend Based on Aromatic Π-Π Stacking and Hydrogen-Bonding Interactions, J. Am. Chem. Soc., 2010, vol. 132, pp. 12051-12058.

Burnworth, M., et al., Optically healable supramolecular polymers, Nature, Apr. 21, 2011, vol. 472, pp. 334-338.

Wojtecki, R.J., et al., Using the dynamic bond to access macroscopically responsive structurally dynamic polymers, Nature Materials, Dec. 15, 2010, vol. 10, pp. 14-27.

Aida, T., et al., Functional Supramolecular Polymers, Science, Feb. 17, 2012, vol. 335, pp. 813-817.

* cited by examiner

DENTAL MATERIALS BASED ON COMPOUNDS HAVING DEBONDING-ON-DEMAND PROPERTIES

CROSS-REFERENCE TO RELATED APPLICATIONS

This application is a National Stage application of International patent application PCT/EP2012/067680 filed on Sep. 10, 2012, which claims priority to European patent application No. 11180645.1 filed on Sep. 8, 2011, the disclosures of which are incorporated herein by reference in their entirety.

The present invention relates to compounds with debonding-on-demand (DoD) properties and their use as components in dental materials, in particular for preparing adhesives and cements.

Adhesive bonds that can be debonded again are increasingly important in various technological fields. Examples are the detachment of components within the framework of automated manufacturing processes, the repair of complex components with adhesively bonded subcomponents or the simplification of the separation of materials when recycling such components at the end of the product's life. The debonding of adhesive bonds can be achieved on demand by significantly reducing the strength of the adhesive bond layer e.g. by heating.

Thus DE 198 32 629 A1 describes an adhesive system for forming reversible adhesive bonds based on polyurethanes, polyureas or epoxy resins, in which an additional component can be activated by introducing energy such that a degradation of the adhesive components takes place. For example, organic bases or acids which bring about a degradation of the adhesive resin can be released from blocked precursors by introducing heat or radiation energy.

WO 2010/128042 A1 describes industrial adhesive compositions for debondable adhesive bonds for aircraft or motor vehicle construction which consist of a customary adhesive matrix and a particulate expansion material such as e.g. azodicarbonamide. The components are debonded by heating the adhesive bond at least to the expansion temperature of the expansion material.

WO 02/46260 A1 and WO 2010/002262 A1 describe supramolecular polymers which can be used as adhesives. When heated, these plastics decompose into liquid, low molecular weight compounds with low viscosity. This process is reversible, with the result that the adhesive is restored when cooled. Thus adhesive bonds can be reversibly created and debonded by heating and cooling.

In dentistry, the debonding of adhesive bonds is important among other things in orthodontics, where brackets which are adhesively bonded to the tooth surface to correct malocclusions must be removed again without damaging the tooth enamel after successful correction. Moreover, in the case of repair or complete replacement of high-strength ceramic restorations or crowns which are laborious to remove mechanically, cement bonds that can be easily softened or separated would be advantageous.

In connection with orthodontic applications, US 2007/0142498 A1 describes dental compositions which contain thermally controllable additives such as e.g. thermoplastic polymers.

US 2007/0142497 A1 describes dental compositions based on dimethacrylates with acid-labile tertiary carbonate groups and photoacids such as e.g. triarylsulphonium salts. These compositions can be photochemically cured with suitable initiators such as for instance the bisacyl phosphine oxide Irgacure 819 with light in the visible range (photobonding) and softened again by irradiation with UV light at increased temperature (photothermal debonding).

It is an object of the invention to provide adhesive dental restorative materials which display good substrate adhesion in particular to the tooth structure and/or dental ceramics and allow a debonding from the substrate by introducing heat, and are thus suitable above all for preparing adhesives or composite cements with debonding-on-demand properties.

This object is achieved according to the invention by dental restorative materials based on a thermolabile compound of Formula I:

$$[(Z^1)_m\text{-}Q^1\text{-}X)]_k\text{-}T\text{-}[Y\text{-}Q^2\text{-}(Z^2)_n]_l \qquad \text{Formula I,}$$

in which

T represents a thermolabile unit which contains at least one thermolabile group based on non-covalent interactions, $Z^1$ and $Z^2$ in each case independently represent a polymerizable group selected from vinyl groups, $CH_2=CR^1-CO-O-$ and $CH_2=CR^1-CO-NR^2-$ or an adhesive group selected from $-Si(OR)_3$, $-COOH$, $-O-PO(OH)_2$, $-PO(OH)_2$, $-SO_2OH$ and $-SH$, $Q^1$ in each case independently is missing or represents an (m+1)-valent linear or branched aliphatic $C_1\text{-}C_{20}$ radical which can be interrupted by $-O-$, $-S-$, $-CO-O-$, $-O-CO-$, $-CO-NR^3-$, $-NR^3-CO-$, $-O-CO-NR^3-$, $-NR^3-CO-O-$ or $-NR^3-CO-NR^3-$, $Q^2$ in each case independently is missing or represents an (n+1)-valent linear or branched aliphatic $C_1\text{-}C_{20}$ radical which can be interrupted by $-O-$, $-S-$, $-CO-O-$, $-O-CO-$, $-CO-NR^3-$, $-NR^3-CO-$, $-O-CO-NR^3-$, $-NR^3-CO-O-$ or $-NR^3-CO-NR^3$, X and Y in each case independently are missing or represent $-O-$, $-S-$, $-CO-O-$, $-O-CO-$, $-CO-NR^3-$, $-NR^3-CO-$, $-O-CO-NR^3-$, $-NR^3-CO-O-$ or $-NR^3-CO-NR^3$, R, $R^1$, $R^2$ and $R^3$ in each case independently represent H or a $C_1\text{-}C_7$ alkyl radical, k and l in each case independently are 0, 1, 2 or 3 and m and n in each case independently are 1, 2 or 3.

In an embodiment, at least one $Z^1$ or $Z^2$ is a polymerizable group and at least one $Z^1$ or $Z^2$ is an adhesive group. In this context those compounds of Formula I in which one of $Z^1$ and $Z^2$ represents a polymerizable group and the other of $Z^1$ and $Z^2$ represents an adhesive group are preferred. It is furthermore preferred that k and l are each independently 1, 2 or 3. In another embodiment, $Z^1$ and $Z^2$ both represent a polymerizable group. In another embodiment, one or both of $Z^1$ and $Z^2$ can be missing.

The indication that a radical can be interrupted by a group, such as for example $-O-$, is to be understood such that the group is inserted into the carbon chain of the radical, i.e. is bordered on both sides by carbon atoms. The number of these groups is therefore at least 1 less than the number of carbon atoms and the groups cannot be terminal. According to the invention, radicals which are not interrupted by the named groups are preferred.

According to the invention, only those compounds which are compatible with the chemical valence theory are considered.

Those compounds of Formula I are particularly preferred in which in each case independently of each other
one of $Z^1$ and $Z^2$ in each case independently represents a polymerizable group selected from $CH_2=CR^1$—CO—O— and $CH_2=CR^1$—CO—$NR^2$— and the other of $Z^1$ and $Z^2$ in each case independently represents a polymerizable group selected from $CH_2=CR^1$—CO—O— and $CH_2=CR^1$—CO—$NR^2$— and preferably an adhesive group selected from —$Si(OR)_3$, —COOH, —O—PO(OH)$_2$, —PO(OH)$_2$, —$SO_2OH$ and —SH, $Q^1$ in each case independently is missing or represents an (m+1)-valent linear or branched aliphatic $C_1$-$C_{10}$ radical which can be interrupted by —O—, —CO—O—, —O—CO—, —CO—$NR^3$—, or —$NR^3$—CO—, $Q^2$ in each case independently is missing or represents an (n+1)-valent linear or branched aliphatic $C_1$-$C_{10}$ radical which can be interrupted by —O—, —CO—O—, —O—CO—, —CO—$NR^3$— or —$NR^3$—CO—, X and Y in each case independently are missing or represent —O—, —CO—O—, —O—CO—, —CO—$NR^3$— or —$NR^3$—CO—, R in each case independently is H, $CH_3$ or $C_2H_5$, $R^1$ in each case independently is H or $CH_3$, $R^2$ in each case independently is H, $CH_3$ or $C_2H_5$, $R^3$ in each case independently is H, $CH_3$ or $C_2H_5$, and/or k, l, m and n in each case independently are 1 or 2.

Compounds in which all the variables each have one of the preferred meanings defined above are particularly preferred.

Suitable thermolabile groups are known per se. They are characterized according to the invention in that they contain one or more thermolabile bonds based on non-covalent interactions such as hydrogen bonds, coordinate bonds, metal-ligand interactions, π-π interactions, donor-acceptor interactions, dipole-dipole interactions, ion-pair interactions, van der Waals interactions, hydrophilic interactions and/or hydrophobic interactions. Preferred thermolabile groups include groups with thermolabile hydrogen bonds between hydrogen bond-forming motifs such as 2-ureido-4[1H]-pyrimidone groups (UPy groups) or their derivatives, groups with thermolabile coordinate bonds or metal-ligand interactions such as complexes of 2,6-bis-benzimidazole-pyridine groups or 2,2':6',2"-terpyridine groups in particular with transition metal or lanthanoid ions as well as thermolabile adducts based on π-π interactions and/or donor-acceptor interactions such as adducts of electron-poor diimide-rich and electron-rich pyrene groups. Examples of thermolabile groups with non-covalent interactions are also described in R. J. Wojtecki et al., *Nature Materials* 2011, 10, 14-27; J. D. Fox et al., *Macromolecules* 2009, 42, 6823; S. Sivakova et al., *Chem. Soc. Rev.* 2005, 34, 9-21 and S. J. Rowan et al., *Faraday Discussions* 2005, 128, 43.

In one embodiment, the thermolabile unit T is a thermolabile group. The thermolabile group preferably has the formula -$T^1$••$T^2$-, in which $T^1$ and $T^2$ represent complementary groups which are connected to each other by thermolabile non-covalent interactions.

In this context dental restorative materials based on a thermolabile polymerizable compound of Formula II are particularly preferred:

Formula II, in which

T represents a thermolabile group, $Z^1$ and $Z^2$ in each case independently represent a polymerizable group selected from vinyl groups, $CH_2=CR^1$—CO—O— and $CH_2=CR^1$—CO—$NR^2$— or an acid group selected from —O—PO(OH)$_2$, —PO(OH)$_2$ and —$SO_2OH$, wherein at least one $Z^1$ or $Z^2$ is a polymerizable group and at least one $Z^1$ or $Z^2$ is an adhesive group, $Q^1$ in each case independently is missing or represents an (m+1)-valent linear or branched aliphatic $C_1$-$C_{10}$ radical which can be interrupted by —O—, —S—, —CO—O—, —O—CO—, —CO—$NR^3$— or —$NR^3$—CO—, $Q^2$ in each case independently is missing or represents an (n+1)-valent linear or branched aliphatic $C_1$-$C_{10}$ radical which can be interrupted by —O—, —S—, —CO—O—, —O—CO—, —CO—$NR^3$— or —$NR^3$—CO—, X and Y in each case independently are missing or represent —O—, —S—, —CO—O—, —O—CO—, —CO—$NR^3$— or —$NR^3$—CO—, $R^1$, $R^2$ and $R^3$ in each case independently represent H or a $C_1$-$C_7$ alkyl radical and k, l, m and n in each case independently are 1, 2 or 3.

In this context those compounds of Formula II in which one of $Z^1$ and $Z^2$ represents a polymerizable group and the other of $Z^1$ and $Z^2$ represents an acid group are preferred.

Those compounds of Formula II are particularly preferred in which in each case independently of each other
one of $Z^1$ and $Z^2$ in each case independently represents a polymerizable group selected from $CH_2=CR^1$—CO—O— and $CH_2=CR^1$—CO—$NR^2$— and the other of $Z^1$ and $Z^2$ in each case independently represents an acid group selected from —O—PO(OH)$_2$ and —PO(OH)$_2$ and —$SO_2OH$, $Q^1$ in each case independently is missing or represents an (m+1)-valent linear or branched aliphatic $C_1$-$C_{10}$ radical which can be interrupted by —O—, —CO—O—, —O—CO—, —CO—$NR^3$— or —$NR^3$—CO—, $Q^2$ in each case independently is missing or represents an (n+1)-valent linear or branched aliphatic $C_1$-$C_{10}$ radical which can be interrupted by —O—, —CO—O—, —O—CO—, —CO—$NR^3$— or —$NR^3$—CO—, X and Y in each case independently are missing or represent —O—, —CO—O—, —O—CO—, —CO—$NR^3$— or —$NR^3$—CO—, $R^1$ in each case independently is H or $CH_3$, $R^2$ in each case independently is H, $CH_3$ or $C_2H_5$,

$R^3$ in each case independently is H, $CH_3$ or $C_2H_5$, and/or k, l, m and n in each case independently are 1 or 2.

Compounds in which all the variables each have one of the preferred meanings defined above are particularly preferred.

In another embodiment, the thermolabile unit T is an oligomeric or polymeric unit which contains at least one thermolabile group and at least one oligomeric, homopolymeric or heteropolymeric chain P. Examples of suitable chains P are vinyl, diene, polycondensation and polyaddition oligomers and polymers, copolymers and mixtures thereof. The chains P preferably have a numerically average molar mass of from 200 to 20000 g/mol and preferably from 1000 to 10000 g/mol. Amorphous oligomeric, homopolymeric and heteropolymeric chains with a glass transition temperature of 0° C. or lower, such as for example ethylene/butylene copolymers, polyethylene oxide or polytetrahydrofuran are particularly preferred.

In particular, those compounds of Formula I are preferred in which the thermolabile unit T has the Formula III or IV:

Formula III,

[—P—($X^1$-Q-$Y^1$-$T^1$-$Y^2$-Q-$X^2$—)$_q$]$_p$

Formula IV, in which

P in each case independently represents an oligomeric, homopolymeric or heteropolymeric chain which preferably has a numerically average molar mass of from 200 to 20000 g/mol, T[1] and T[2] represent groups which can be identical or different and are connected to each other by thermolabile non-covalent interactions, Q in each case independently is missing or represents a divalent linear, branched and/or cyclic $C_1$-$C_{20}$ radical which can be fully or partly unsaturated and/or aromatic and can be interrupted by —O—, —S—, —CO—O—, —O—CO—, —CO—NR[3]—, —NR[3]—CO—, —O—CO—NR[3]—, —NR[3]—CO—O— or —NR[3]—CO—NR[3]—, $X^1$ and $X^2$ in each case independently are missing or represent —O—, —S—, —CO—O—, —O—CO—, —CO—NR[3]—, —NR[3]—CO—, —O—CO—NR[3]—, —NR[3]—CO—O— or —NR[3]—CO—NR[3]—, $Y^1$ and $Y^2$ in each case independently are missing or represent —O—, —S—, —CO—O—, —O—CO—, —CO—NR[3]—, —NR[3]—CO—, —O—CO—NR[3]—, —NR[3]—CO—O— or —NR[3]—CO—NR[3]—, and p independently is 1 to 100 and q independently is 1, 2, 3 or 4.

Those units T are particularly preferred in which in the Formulae III and IV in each case independently of each other P in each case independently represents an oligomeric, homopolymeric or heteropolymeric chain which preferably has a numerically average molar mass of from 1000 to 10000 g/mol, Q in each case independently is missing or represents a divalent linear or branched $C_1$-$C_{10}$ radical which can be interrupted by —O—, —S—, —CO—O—, —O—CO—, —CO—NR[3]—, —NR[3]—CO—, —O—CO—NR[3]—, —NR[3]—CO—O— or —NR[3]—CO—NR[3]—, $X^1$ and $X^2$ in each case independently are missing or represent —O—, —S—, —CO—O—, —O—CO—, —CO—NR[3]—, —NR[3]—CO—, —O—CO—NR[3]—, —NR[3]—CO—O— or —NR[3]—CO—NR[3]—, $Y^1$ and $Y^2$ in each case independently are missing or represent —O—, —S—, —CO—O—, —O—CO—, —CO—NR[3]—, —NR[3]—CO—, —O—CO—NR[3]—, —NR[3]—CO—O— or —NR[3]—CO—NR[3]—, p independently is 1 to 50, in particular 5 to 50 and particularly preferably 10 to 50 and q independently is 1 or 2 and in particular 1.

Compounds in which all the variables each have one of the preferred meanings defined above are particularly preferred.

Compounds of Formula I in which the thermolabile unit T is capable of forming supramolecular motifs are preferred according to the invention. Such supramolecular motifs can be formed by association of two or more chemical species by means of non-covalent intermolecular interactions (Supramolecular Chemistry, J.-M. Lehn, Wiley-VCH, 1995 and Supramolecular Chemistry: From Molecules to Nanomaterials, P. A. Gale and J. W. Steed (Eds.), Wiley, 2012). Such association processes are the basis for the formation of supramolecular polymers in which individual polymer chains are held together by the non-covalent bonds described above (Tom F. A. de Greef et al., *Nature* 2008, 453, 171-173; T. Aida et al., *Science* 2012, 335, 813-817). As a rule, non-covalent bonds are weaker and more dynamic than covalent bonds. Their formation is therefore often reversible, with the result that they can be broken and reformed as often as required, for example by raising the temperature, reducing the concentration, or increasing the polarity of a solvent. Such supramolecular motifs are particularly suitable as thermolabile units.

In particular, those compounds of Formula I are preferred in which the thermolabile group -T[1]••T[2]- is selected from the group consisting of:

wherein:

$R^4$ is H or a $C_1$-$C_{10}$ alkyl radical and

M represents a transition metal ion or lanthanoid ion such as for example $Zn^{2+}$, $La^{3+}$ or $Eu^{3+}$.

It was surprisingly found that the dental restorative materials according to the invention which comprise at least one thermolabile compound of Formula I on the one hand display excellent mechanical properties as well as an excellent adhesion to the tooth structure and dental ceramics and on the other hand can be easily debonded from the substrate by the direct or indirect introduction of heat.

Thermolabile polymerizable compounds which contain thermolabile groups can be prepared by the reaction of suitably functionalized groups $T^1$ or $T^2$ with complementarily functionalized monomers.

Thus for example the 2-ureido-4[1H]-pyrimidone (UPy) derivative UPy-$CH_2CH_2OC(O)C(CH_3)CH_2$ can be obtained by reaction of 2-isocyanatoethyl methacrylate and 6-methylisocytosine (2-amino-4-hydroxy-6-methylpyrimidone):

To prepare the 2,6-bis(1-methylbenzimidazolyl)-4-hydroxypyridine (Mebip) derivative [Zn(Mebip-$CH_2CH_2OC$ $(O)C(CH_3)CH_2)_2](ClO_4)_2$, first 2,6-bis-(1-methylbenzimidazolyl)-4-hydroxypyridine can be etherified with bromoethanol, e.g. by heating in dimethylformamide in the presence of $K_2CO_3$, and methacryloyl chloride can then be added to the thus-prepared Mebip-$CH_2CH_2OH$, e.g. in the presence of triethylamine in dichloromethane. A salt of a transition metal or lanthanoid such as for example $Zn(ClO_4)_2$ can then be added to the thus-obtained Mebip-$CH_2CH_2OC$ $(O)C(CH_3)CH_2$ in order to obtain the desired product with a thermolabile group:

pyrimidinone groups, which is suitable for the formation of hydrogen bonds (B. J. B. Folmer et al., *Adv. Mater.* 2000, 12, 874).

Conversely, α,ω-OH-terminated oligomers or polymers can first be reacted with an excess of a compound in which a linker group is bonded at both ends to a functional group which can react with hydroxyl groups, for example an isocyanate group. The thus-obtained α,ω-OH-functionalized oligomer or polymer can then be reacted with a compound in which a group $T^1$ or $T^2$ is covalently bonded to a functional group such as a hydroxyl group.

Example: Reaction of an α,ω-OH-terminated polymer with an excess of diphenylmethane-4,4'-diisocyanate (MDI) and reaction of the obtained α,ω-isocyanate-terminated polymer with 2-aminomethylpyrene to form a polymer terminally functionalized in each case with pyrene groups, which can form π-π interactions and/or donor-acceptor interactions with electron-poor diimide groups (S. Burattini et al., *J. Am. Chem. Soc.* 2010, 132, 12051).

Alternatively, α,ω-OH-terminated oligomers or polymers can be reacted for example by means of the Mitsunobu reaction with a compound in which a group $T^1$ or $T^2$ is covalently bonded to a functional group such as a hydroxyl group.

Example: Reaction of an α,ω-OH-terminated polymer with 2,6-bis(1'-methylbenzimidazolyl)-4-hydroxy-pyridine to form a polymer terminally functionalized in each case with 2,6-bis(1'-methylbenzimidazolyl)pyridine groups, which is suitable for the formation of a coordinate bond accompanied by complexing of transition metal or lanthanoid ions (Burnworth, M. et al. *Nature* 2011, 472, 334).

In an analogous manner, further α,ω-OH-terminated oligomer or polymer can first be functionalized at one end with a group $T^1$ or $T^2$ and then functionalized at the other end with The properties of the thermolabile group can be influenced in a targeted manner by the choice of the metal salt.

The compounds according to the invention of Formula I with an oligomeric or polymeric thermolabile unit T can be prepared analogously to synthesis methods known per se.

Thus α,ω-OH-terminated oligomers or polymers, such as polysiloxanes, polyethers, polyesters or polycarbonates, can be reacted with an excess of a compound in which a group $T^1$ or $T^2$ is covalently bonded to a functional group which can react with hydroxyl groups, for example an isocyanate group.

Example: Reaction of an α,ω-OH-terminated polymer with an excess of 2-(6-isocyanatohexylaminocarbonylamino)-6-methyl-4[1H]pyrimidinone to form a polymer terminally functionalized in each case with 2-ureido-4[1H]- a polymerizable group or an adhesive group, or vice versa. The thus-obtained mixed functionalized oligomer or polymer can then, together with an oligomer or polymer functionalized at both ends with groups $T^1$ or $T^2$ be converted to a compound of Formula I in a manner known per se.

Alternatively, to prepare compounds according to the invention of Formula I with an oligomeric or polymeric thermolabile unit T, thermolabile polymerizable compounds which contain thermolabile groups can be prepared as described above and reacted for example by copolymerization with monofunctional methacrylate monomers.

The dental materials according to the invention preferably comprise, in addition to the thermolabile compound of Formula I, one or more (additional) radically polymerizable monomers (comonomers), in particular mono- or polyfunctional (meth)acrylic acid derivatives. By monofunctional (meth)acrylic acid derivatives are meant compounds with one (meth)acrylic acid group, by polyfunctional (meth)acrylic acid derivatives are meant compounds with two or more, preferably 2 to 4, (meth)acrylic acid groups. Polyfunctional monomers have a cross-linking effect.

Preferred mono- or polyfunctional (meth)acrylic acid derivatives according to the invention are methyl, ethyl, hydroxyethyl, butyl, benzyl, tetrahydrofurfuryl or isobornyl (meth)acrylate, bisphenol-A-di(meth)acrylate, bis-GMA (an addition product of methacrylic acid and bisphenol-A-diglycidyl ether), UDMA (an addition product of 2-hydroxyethyl methacrylate (HEMA) and 2,2,4-trimethylhexamethylene diisocyanate), di-, tri- or tetraethylene glycol di(meth)acrylate, trimethylolpropane tri(meth)acrylate, pentaerythritol tetra(meth)-acrylate, glycerol di(meth)acrylate, 1,4-butanediol di(meth)acrylate, 1,10-decanediol di(meth)acrylate and 1,12-dodecanediol di(meth)-acrylate.

Particularly preferred mono or polyfunctional (meth)acrylic acid derivatives are N-mono- or disubstituted acrylamides such as N-ethylacrylamide, N,N-dimethacrylamide, N-(2-hydroxyethyl)acrylamide or N-methyl-N-(2-hydroxyethyl)acrylamide, N-monosubstituted methacrylamides such as N-ethylmethacrylamide or N-(2-hydroxyethyl)methacrylamide as well as N-vinylpyrrolidone and allyl ether. These monomers are characterized by a high hydrolysis stability and are particularly suitable as diluting monomers because of their relatively low viscosity.

Preferred polyfunctional (meth)acrylic acid derivatives with high hydrolysis stability are cross-linking pyrrolidones such as 1,6-bis(3-vinyl-2-pyrrolidonyl)-hexane, bisacrylamides such as methylene or ethylene bisacrylamide and bis(meth)acrylamides such as N,N'-diethyl-1,3-bis(acrylamido)-propane, 1,3-bis(methacrylamido)-propane, 1,4-bis(acrylamido)-butane or 1,4-bis(acryloyl)-piperazine which can be synthesized by reacting the corresponding diamines with (meth)acrylic acid chloride.

Thermolabile cross-linking monomers are also particularly suitable according to the invention as comonomers. By these are meant cross-linking monomers which have at least one thermolabile covalent group between two polymerizable groups. Examples are polyfunctional (meth)acrylates or (meth)acrylamides with at least one thermolabile group between two (meth)acrylic groups. Coming into consideration as thermolabile covalent groups are in particular thermolabile cycloaddition adducts such as Diels-Alder adducts, hetero-Diels-Alder adducts as well as thermolabile alkoxyamine, oxime-ester, oxime-urethane or azo groups. Examples are Diels-Alder adducts such as the Diels-Alder adduct from furfuryl methacrylate and N-(3-(methacryloyloxy)propyl)-maleinimide, the reaction products of N-hydroxy-(meth)acrylamide with di- or triisocyanates such as hexamethylene-1,6-diisocyanate (HDI), 2,2,4-trimethylhexamethylene-1,6-diisocyanate or the HDI trimer, as well as products which are obtained by stoichiometric reaction of di- or triisocyanates with 1-hydroxymethylacrylic esters such as 1-hydroxymethyl ethyl acrylate or with β-keto ester (meth)acrylates such as 2-acetoacetoxyethyl methacrylate. Gas-releasing thermolabile cross-linking monomers are also particularly suitable. Examples are the esterification products of azobis(4-cyanovaleric acid) with hydroxyalkyl (meth)acrylates such as hydroxyethyl (meth)acrylate or hydroxypropyl (meth)acrylate or with N-(hydroxyalkyl) (meth)acrylamides such as N-(5-hydroxypentyl) methacrylamide or N-methyl-N-(2-hydroxyethyl) acrylamide.

In addition to the thermolabile compound of Formula I and optionally the above-named comonomers, the dental restorative materials according to the invention can preferably also comprise radically polymerizable, acid group-containing monomers (adhesive monomers). Preferred acid groups are carboxylic acid groups, phosphonic acid groups, phosphoric acid groups and sulphonic acid groups.

Preferred monomers with polymerizable carboxylic acids are maleic acid, acrylic acid, methacrylic acid, 2-(hydroxymethyl)acrylic acid, 4-(meth)acryloyloxyethyltrimellitic anhydride, 10-methacryloyloxydecylmalonic acid, N-(2-hydroxy-3-methacryloyloxypropyl)-N-phenylglycine and 4-vinylbenzoic acid.

Preferred monomers with polymerizable phosphonic acid groups are vinyl phosphonic acid, 4-vinylphenyl phosphonic acid, 4-vinylbenzyl phosphonic acid, 2-methacryloyloxyethyl phosphonic acid, 2-methacrylamidoethyl phosphonic acid, 4-methacrylamido-4-methyl-pentyl phosphonic acid, 2-[4-(dihydroxyphosphoryl)-2-oxa-butyl]-acrylic acid, 2-[4-(dihydroxyphosphoryl)-2-oxa-butyl]-acrylic acid ethyl and -2,4,6-trimethylphenyl ester.

Preferred monomers with polymerizable phosphoric acid groups are 2-methacryloyloxypropyl mono- or dihydrogen phosphate, 2-methacryloyloxyethyl mono- or dihydrogen phosphate, 2-methacryloyloxyethyl-phenyl hydrogen phosphate, dipentaerythritolpentamethacryloyloxy phosphate, 10-methacryloyloxydecyl dihydrogen phosphate, phosphoric acid mono-(1-acryloyl-piperidin-4-yl)-ester, 6-(methacrylamido)hexyl dihydrogen phosphate and 1,3-bis-(N-acryloyl-N-propyl-amino)-propan-2-yl-dihydrogen phosphate.

Preferred monomers with polymerizable sulphonic acid groups are vinylsulphonic acid, 4-vinylphenylsulphonic acid and 3-(methacryl-amido)propylsulphonic acid.

Preferably, mixtures of the compound of Formula I and in particular Formula II with the above-named monomers are used. Based on the total weight of the mixture, preferred mixtures comprise:

1 to 90 wt.-%, preferably 5 to 80 wt.-%, particularly preferably
5 to 70 compound of Formula I,
0 to 70 wt.-%, preferably 1 to 60 wt.-%, particularly preferably
5 to 50 and quite particularly preferably 10 to 30 wt.-% comonomer and in particular mono- and/or polyfunctional (meth)acrylates,
0 to 70 wt.-%, preferably 1 to 60 wt.-% and particularly preferably
5 to 50 wt.-% thermolabile cross-linking monomer and
0 to 40 wt.-%, preferably 1 to 30 wt.-% and particularly preferably
5 to 20 wt.-% adhesive monomer.

Particularly preferred mixtures (in each case based on the total weight of the mixture) are given in the following table:

| | Component (wt.-%) | | | | | |
|---|---|---|---|---|---|---|
| | A | B | C | D | E | F |
| Compound of Formula I, in particular of Formula II | 1-90 | 5-80 | 5-70 | 5-70 | 5-70 | 5-70 |
| Comonomer, in particular mono- and/or polyfunctional (meth)acrylate | 0-70 | 0-60 | 1-60 | 5-60 | 5-50 | 0-30 |
| Thermolabile cross-linking monomer | 0-70 | 0-50 | 0-50 | 5-50 | 5-50 | 5-50 |
| Adhesive monomer | 0-40 | 0-30 | 0-30 | 0-20 | 0-20 | 0-30 |

Moreover, the dental restorative materials according to the invention preferably also comprise an initiator for radical polymerization.

Preferably, benzophenone, benzoin and their derivatives or α-diketones or their derivatives, such as 9,10-phenanthrenequinone, 1-phenyl-propane-1,2-dione, diacetyl or 4,4'-dichlorobenzil are used to initiate radical photopolymerization. Camphorquinone and 2,2-dimethoxy-2-phenylacetophenone are particularly preferably used, and quite particularly preferably α-diketones combined with amines, such as 4-(dimethylamino)-benzoate, N,N-dimethylaminoethyl methacrylate, N,N-dimethyl-sym.-xylidine or triethanolamine as reductants. Norrish type I photoinitiators, in particular acyl or bisacylphosphine oxides, monoacyltrialkyl- or diacyldialkylgermanium compounds, such as benzoyltrimethylgermanium, dibenzoyldiethylgermanium or bis-(4-methoxybenzoyl)diethylgermanium are also particularly suitable. Mixtures of the different photoinitiators can also be used, such as for example dibenzoyldiethylgermanium combined with camphorquinone and 4-dimethylaminobenzoic acid ethyl ester.

Preferably, redox-initiator combinations, such as for example combinations of benzoyl peroxide with N,N-dimethyl-sym.-xylidine or N,N-dimethyl-p-toluidine, are used as initiators for a polymerization carried out at room temperature. Furthermore, redox systems consisting of peroxides and reductants such as e.g. ascorbic acid, barbiturates or sulphinic acids, are also particularly suitable.

The dental restorative materials according to the invention can also comprise a thermally gas-releasing additive. Suitable gas-releasing additives are e.g. azo compounds such as azodicarbonamide, 2,2'-azobisisobutyronitrile or 2,2'-azobis(4-cyanopentanoic acid), N-nitroso compounds, hydrazides such as benzenesulphonyl hydrazide, peroxides such as dicumol peroxide or acetone dicarboxylic acid. Examples of such compounds are described for instance in St. Quinn, *Plastics, Additives & Compounding* 2001, 3, 16-21. The decomposition temperature, for example in the case of azo compounds, can be set in a manner known per se by the substituent pattern (cf. D. Braun, R. Jakobi, *Monatshefte Chemie* 1982, 113, 1403-1414).

Furthermore, the dental restorative materials according to the invention can comprise an additive which can convert radiated electromagnetic radiation into heat. Such so-called radiation-to-heat converters are organic, inorganic or organometallic substances or hybrid components which are capable of converting UV, NIR or IR radiation, visible light, microwave or radiowave radiation into heat in order to cleave thermolabile groups. Examples of this are dyes and pigments that absorb UV, NIR or IR radiation. Examples of dyes that absorb in the IR range are azo, methine, anthraquinone or porphyrin dyes. Examples of pigments that absorb NIR radiation are antimony and indium tin oxide, phthalocyanine pigments, soot, Ni and Pt dithiolene complexes. Examples of compounds that absorb in the UV range are benzotriazoles, triazines, benzophenones, cyanoacrylates, salicylic acid derivatives and hindered amine light stabilizers (HALS). Examples of additives that absorb in the frequency range of microwaves (1 to 300 GHz) or radiowaves (10 kHz to 1 GHz) are ferromagnetic ceramic substances, so-called ferrites, which are composed of the iron oxides haematite ($Fe_2O_3$) or magnetite ($Fe_3O_4$) and further oxides for example of the metals Zn, Mn, or Ni and are commercially available as powders.

The dental restorative materials according to the invention furthermore preferably also comprise organic or inorganic filler particles to improve the mechanical properties or to adjust the viscosity. Preferred inorganic particulate fillers are amorphous spherical materials based on oxides, such as $ZrO_2$ and $TiO_2$ or mixed oxides of $SiO_2$, $ZrO_2$ and/or $TiO_2$ with an average particle size of from 0.005 to 2 μm, preferably 0.1 to 1 μm, nanoparticulate or microfine fillers such as pyrogenic silicic acid or precipitated silica with an average particle size of from 5 to 200 nm, preferably 10 to 100 nm, minifillers such as quartz, glass ceramic or glass powders with an average particle size of from 0.01 to 10 μm, preferably 0.1 to 1 μm, as well as X-ray-opaque fillers such as ytterbium trifluoride or nanoparticulate tantalum(V) oxide or barium sulphate with an average particle size of from 10 to 1000 nm, preferably 100 to 300 nm.

Moreover, the dental restorative materials according to the invention can comprise further additives, in particular solvents such as water or ethanol or corresponding solvent mixtures as well as for example stabilizers, flavourings, dyes, microbiocidal active ingredients, fluoride ion-releasing additives, optical brighteners or plasticizers.

Dental restorative materials based on a thermolabile compound of Formula I and in particular of Formula II which comprise the following components are particularly preferred:

a) 0.1 to 50 wt.-%, in particular 1 to 40 wt.-%, preferably 2 to 30 wt.-% and particularly preferably 5 to 30 wt.-% compound of Formula I and in particular of Formula II,
b) 0.01 to 10 wt.-%, preferably 0.1 to 3.0 wt.-% and particularly preferably 0.2 to 2 wt.-% initiator,
c) 0 to 80 wt.-%, preferably 1 to 60 wt.-% and particularly preferably 5 to 50 wt.-% comonomer,
d) 0 to 30 wt.-%, preferably 0.5 to 15 wt.-% and particularly preferably 1 to 5 wt.-% adhesive monomer,
e) 0 to 80 wt.-% filler,
f) 0 to 70 wt.-% solvent.

The preferred filler content depends on the desired use. Adhesives preferably comprise 0 to 20 wt.-% and cements and composites preferably 20 to 80 wt.-% filler.

The same also applies to the solvent content. Adhesives preferably comprise 0 to 60 wt.-% and particularly preferably 1 to 50 wt.-% solvent. Dental materials which comprise water as solvent are preferred. Dental materials which comprise 0 to 20 wt.-% and in particular 1 to 10 wt.-% water are particularly preferred.

The debonding properties of the dental restorative materials according to the invention can be influenced in a targeted manner by the composition of the materials. The adjustment of a composition suitable for a particular purpose belongs to the general knowledge and abilities of a person skilled in the art. Thus, the ability to debond on demand by heating increases with the concentration used of thermolabile components, i.e. in particular the thermolabile compound of Formula I as well as optionally the thermolabile cross-linking monomers and gas-releasing additives. Furthermore, the debonding properties can also be varied by the selection of the comonomers, wherein the cross-linking density and thus also the strength and the elastic modulus can be varied with the proportion of cross-linking monomers or by addition of monofunctional monomers.

The dental materials according to the invention based on the thermolabile compound of Formula I can be used in particular to reversibly attach for example brackets, crowns or veneers.

Preferably, a bond is initially formed by curing materials (adhesive or cement) based on the thermolabile compound of Formula I. Alternatively, the oligomeric or polymeric thermolabile compounds according to the invention of Formula I can also be used directly, for example in the form of a powder, wherein in order to form a bond they are heated briefly to a temperature which lies above the temperature at which the cleavage of the thermolabile bonds sets in. The energy can be introduced by means of electromagnetic radiation. For this, an oligomeric or polymeric thermolabile compound of Formula I is preferably combined with an additive which can convert the irradiated electromagnetic radiation into heat. According to a preferred embodiment, a targeted introduction of energy takes place via an IR radiation source or a laser. According to another preferred embodiment, the energy is introduced by means of UV radiation, in particular with a wavelength in the range of from 320 to 390 nm, preferably in the presence of a UV absorber. Moreover, an inductive heating can be achieved by the action of an alternating magnetic field when ferromagnetic particles such as for example ferromagnetic nanoparticles are incorporated into the dental materials according to the invention. For debonding, the adhesively bonded parts must likewise, in particular as described above, be heated briefly to a temperature which lies above the temperature at which the cleavage of the thermolabile bonds sets in.

A subject of the invention is also the use of a thermolabile compound of Formula I or of a composition as described above as dental restorative material or for the preparation of dental restorative materials, preferably adhesives or cements, particularly preferably self-etching adhesives or cements.

A subject of the invention is furthermore also the use of a thermolabile compound of Formula I or a composition as described above as reversible adhesive or self-healing plastic material or for producing a reversible adhesive or self-healing plastic material.

The invention is explained in more detail below by means of examples.

EXAMPLES

Example 1

Synthesis of an Oligomeric Thermolabile Hydrogen Bond Compound UPy-Kraton

Hydroxy-terminated hydrogenated poly(ethylene-co-butylene) (Krasol HLBH-P 3000, Cray Valley, average molar mass 3500 g/mol, 10.0 g) was dried for 2 days in a vacuum drying oven at 65° C. and 400 mbar and then dissolved in 100 ml anhydrous chloroform by stirring under nitrogen atmosphere. 2(6-Isocyanatohexylaminocarbonylamino)-6-methyl-4[1H]pyrimidine (UPy isocyanate, 3.32 g, 11.3 mmol) was dissolved in 30 ml dry chloroform and added to the Krasol solution, and the reaction mixture was heated to 40° C. 2 drops dibutyltin dilaurate were then added as catalyst and the mixture was heated and stirred under reflux for 16 h. After cooling to 50° C., 3 g 3-aminopropylsilicate was added and the reaction mixture was heated again and stirred under reflux for 3 h. The reaction mixture was then cooled to room temperature and stirred overnight. The mixture was centrifuged at room temperature (7000 rpm, 5 min), the solid constituents were separated off and the residue was washed twice with chloroform. The organic phases were combined and the solvent was separated off on a rotary evaporator. The crude product was then dried overnight under high vacuum at room temperature. 9.78 g (76% yield) UPy-Kraton was obtained as transparent, rubbery solid.

$^1$H-NMR (360 MHz, CDCl$_3$): δ=13.14 (s, 1H), 11.88 (s, 1H), 10.12 (s, 1H), 5.86 (s, 1H), 4.84 (s, 1H), 4.06 (s, 3H), 3.20 (m, 8H), 2.23 (s, 6H, CH3), 1.67-0.92 (m, 436H), 0.92-0.50 (m, 132H).

$^{13}$C-NMR (91 MHz, CDCl$_3$): δ=183.06, 148.47, 135.73, 107.11, 103.50, 39.27, 38.81, 38.27, 36.50, 33.89, 33.64, 31.08, 30.62, 30.16, 27.18, 26.99, 26.83, 26.44, 26.27, 11.28, 11.05, 10.95, 10.78, 10.67, 10.35.

IR (cm$^{-1}$): 2959, 2921, 2872, 2852, 2270, 1700, 1666, 1589, 1527, 1460, 1379, 1304, 1254, 1139, 1041, 942, 843, 761, 744, 721, 621, 612, 602, 593, 586.

GPC: $M_n$=4000 g/mol, $M_w$=7600 g/mol, polydispersity ($M_w/M_n$): 1.90.

Example 2

Cementing Tooth Crowns with UPy-Kraton from Example 1

5 Straumann Anatomical IPS e.max abutments (Ivoclar Vivadent AG) were each mounted on lab analogs for the cemented and removable prosthesis, cut to a stump height of 4 mm and the stump ends rounded. To fit these, 5 milled crowns were produced from e.max ZirCAD (Ivoclar Vivadent AG) with a cement gap of 100 μm being set. UPy-Kraton from Example 1 was ground to a powder accompanied by cooling. The crowns were filled with 20 mg pulverized UPy-Kraton and maintained at a temperature of 80° C. for 5 min. The UPy Kraton melted in the process. The abutments, likewise maintained at a temperature of 80° C., were then inserted into the crowns from above accompanied by gentle turning. In order to complete the bond, the cemented crowns were loaded with 20 N at 80° C. for 3 min and then cooled to room temperature for at least 10 min with the load being maintained. The peeling forces were measured at the earliest 1 h after sample preparation.

To measure the peeling forces, the crowns were clamped in a universal tensile testing machine (Zwick-Roell Z010). The crowns were then pulled off the abutment at a constant speed of 1.0 mm/min and the maximum force occurring in each case was recorded. A peeling force of 103.0±23.7 N was measured.

By heating the cemented crowns to 80° C., they were able to be removed from the stumps without force.

Example 3A (Comparison)

Optical Bonding of Transparent Substrates with UPy-Kraton from Example 1

UPy-Kraton from Example 1 was processed to form an approx. 90 μm thin film which was placed on a surface of approx. 10×10 mm between two quartz glasses. The site to be bonded was irradiated with UV light from a point light source (Dr. Hoenle, wavelength range λ=320-390 nm, intensity 900 mW cm$^{-1}$) with pulses of 2×60 s. No adhesive bond was achieved.

Example 3B

Optical Bonding of Transparent Substrates with a Mixture of UPy-Kraton from Example 1 and a UV Absorber UPy-Kraton from Example 1 was mixed with 0.25 wt.-% of the UV absorber 2-(5-chloro-2H-benzotriazol-2-yl)-6-(1,1-dimethylethyl)-4-methylphenol (Tinuvin 326, Ciba). This mixture was processed to form an approx. 90 μm thin film which was placed on a surface of approx. 10×10 mm between two quartz glasses. The site to be bonded was irradiated with UV light from a point light source (Dr. Hoenle, wavelength range λ=320-390 nm, intensity 900 mW cm$^{-1}$) with pulses of 2×60 s. An air bubble-free bond with good adhesion between the two substrates was achieved. The peeling forces were measured in a universal tensile testing machine (Zwick-Roell Z010). A peeling force of approximately 1 MPa was measured.

Figure 1:
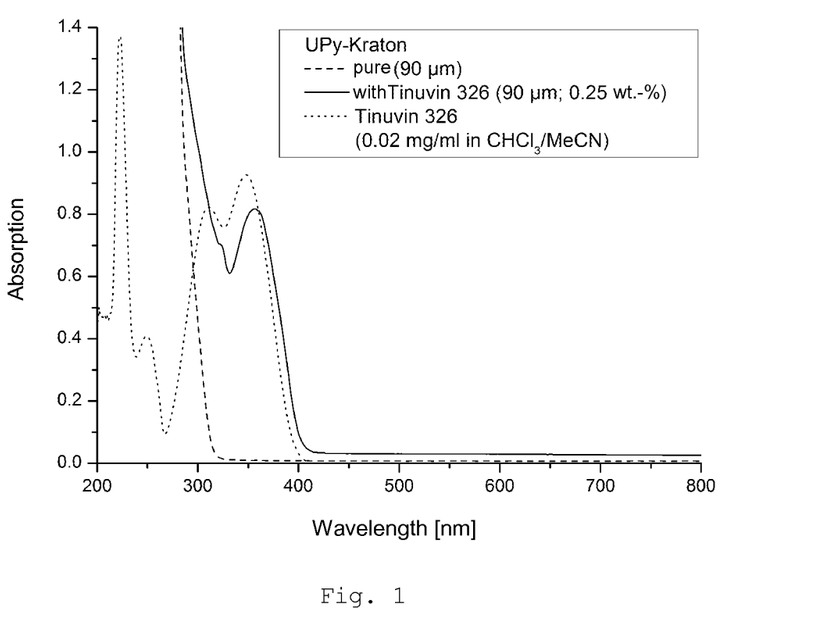
FIG. 1 and FIG. 3 show UV-VIS absorption spectrum of the film.

FIG. 1 shows UV-Vis absorption spectra of approx. 90 μm thin films made of UPy-Kraton from Example 1 ("pure") and a mixture of UPy-Kraton from Example 1 with 0.25 wt.-% of the UV absorber Tinuvin 326 ("with Tinuvin 326") as well as a solution of 0.02 mg/ml Tinuvin 326 in a mixture of chloroform and acetonitrile ("Tinuvin 326").

Figure 2:
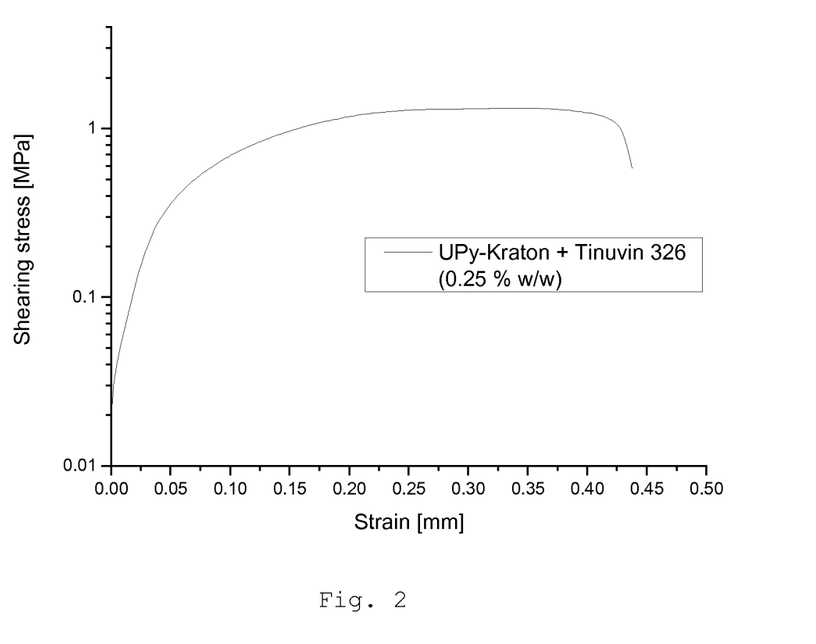
FIG. 2 and FIG. 4 show tensile property of the adhesive bond.

FIG. 2 shows the result of the tensile test on the adhesive bond from Example 3B.

Example 3C (Comparison)

Optical Debonding of an Adhesive Bond of Transparent Substrates with UPy-Kraton from Example 1

UPy-Kraton from Example 1 was processed to form an approx. 90 μm thin film which was placed on a surface of approx. 10×10 mm between two quartz glasses. The site to be bonded was heated by means of a heat gun until an air bubble-free bond formed. A good adhesion between the two substrates was achieved. The peeling forces were measured in a universal tensile testing machine (Zwick-Roell Z010). A peeling force of approximately 1.1 MPa was measured.

The sample was then clamped in a universal tensile testing machine (Zwick-Roell 2010) and tensioned so that a force of approximately 53 N acted on the adhesive joint. The adhesive joint was irradiated with UV light from a point light source (Dr. Hoenle, wavelength range λ=320-390 nm; intensity 900 mW cm$^{-1}$) for 300 s. However, the adhesive bond was not debonded.

Example 3D

Optical Debonding of an Adhesive Bond of Transparent Substrates with a Mixture of UPy-Kraton from Example 1 and a UV Absorber

UPy-Kraton from Example 1 was mixed with 0.25 wt.-% of the UV absorber 2-(5-chloro-2H-benzotriazol-2-yl)-6-(1,1-dimethylethyl)-4-methylphenol (Tinuvin 326, Ciba). This mixture was processed to form an approx. 90 μm thin film which was placed on a surface of approx. 10×10 mm between two quartz glasses. The site to be bonded was heated by means of a heat gun until an air bubble-free bond formed. A good adhesion between the two substrates was achieved.

The sample was then clamped in a universal tensile testing machine (Zwick-Roell 2010) and tensioned such that a force of approximately 30 N acted on the adhesive joint. The adhesive joint was irradiated with UV light from a point light source (Dr. Hoenle, wavelength range λ=320-390 nm; intensity 900 mW cm$^{-1}$). The adhesive bond was debonded after only approximately 30 s.

Example 4

Synthesis of the Thermolabile Metal-ligand Complex [$Zn_{0.8}$BKB]($NTf_2$)$_{1.6}$ Step 1: Synthesis of the Bifunctional Ligand BKB ([2,6-bis-(1-methyl-1H-benzimidazol-2-yl)-pyridin-4-yloxy]-terminated hydrogenated poly(ethylene-co-butylene))

Diethylazodicarboxylate (DEAD, 5 ml, 40 wt.-% in toluene) was added to a solution of 2,6-bis-(1-methyl-1H-benzimidazolyl)-4-hydroxypyridine (2.30 g, 6.47 mmol), triphenylphosphine (3.40 g, 13.0 mmol) and hydroxy-terminated hydrogenated poly(ethylene-co-butylene) (Krasol HLBH-P 3000, Cray Valley, average molar mass 3500 g/mol, 9.1 g) in dry THF (120 ml) at −40° C. and the mixture was stirred. After 4 h, the temperature was raised slowly to 25° C. and the reaction mixture was stirred for a further 44 h. The solvents were then removed under vacuum and the crude product was dissolved in hot hexane (150 ml). The solution was washed three times with methanol and three times with 1M NaOH. The crude product was purified by chromatography ($CH_2Cl_2$, SiOH) and dried overnight, as a result of which BKB was obtained as a white, sticky solid (9.0 g, 81% yield).

$^1$H-NMR (360 MHz, $CDCl_3$): δ=8.05 (s, 4H), 7.94 (s, 4H), 7.54-7.37 (m, 13H), 4.39-4.16 (m, 18H), 1.96-0.95 (m, 477H), 0.95-0.54 (m, 148H).

$^{13}$C-NMR (91 MHz, $CDCl_3$): δ=175.60, 167.14, 151.83, 148.96, 142.45, 136.42, 126.95, 121.79, 110.29, 107.24, 39.02, 38.52, 38.04, 36.26, 33.39, 30.81, 30.36, 29.90, 26.93, 26.74, 26.26, 26.19, 26.02, 11.03, 10.82, 10.79.

GPC: $M_n$=3700 g/mol, $M_w$=4700 g/mol, polydispersity ($M_w/M_n$)=1.27.

UV-Vis titration: $M_n$=4400 g/mol.

NMR spectroscopy: $M_n$=4800 g/mol.

Figure 3:
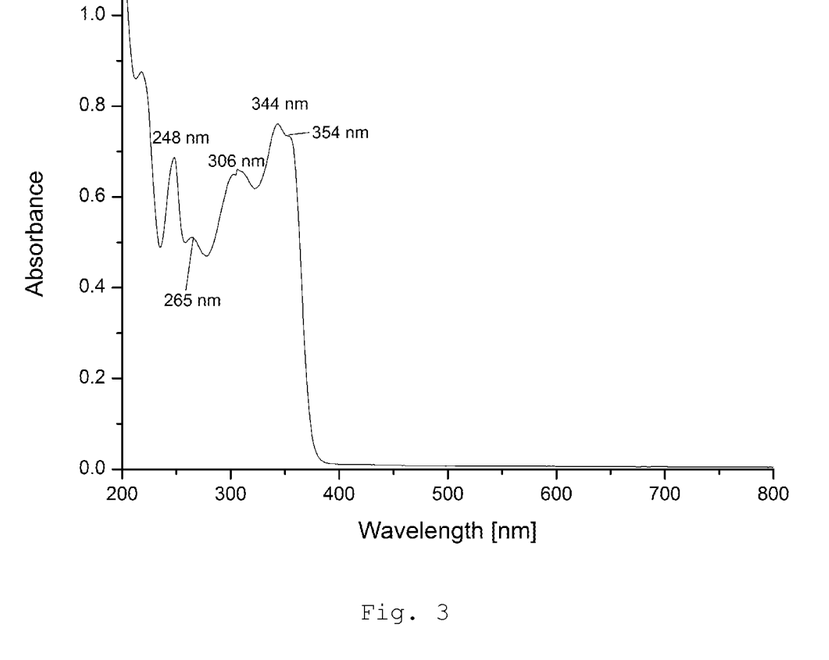

Step 2: Synthesis of the Polymeric Metal-ligand Complex [Zn$_{0.8}$BKB](NTf$_2$)$_{1.6}$ Zinc(II) trifluoromethane sulphonamide (Zn(NTf$_2$)$_2$, 116.6 mg) was dissolved in dry acetonitrile (MeCN, 10 ml). The exact concentration of Zn$^{2+}$ in the solution was determined by UV-Vis titration with C$_{12}$BIP (2,6-bis-(1-methyl-1H-benzimidazolyl)-4-dodecyloxy-pyridine). BKB (2.01 g) was dissolved in chloroform (7 ml, dried over basic Al$_2$O$_3$) and the corresponding quantity of the Zn(NTf$_2$)$_2$ solution was added dropwise accompanied by careful stirring. After 10 min of further stirring, the solvent was removed under vacuum and the product was dried further overnight. The obtained product was hot-pressed in order to obtain a film. A UV spectrum thereof was recorded. FIG. 3 shows the UV-VIS absorption spectrum of the thus-obtained film.

Example 5

Cementing Tooth Crowns with [Zn$_{0.8}$BKB](NTf$_2$)$_{1.6}$ from Example 4

Analogously to Example 2, milled crowns made of e.max ZirCAD were cemented to Straumann Anatomical IPS e.max abutments, wherein the crowns were filled with [Zn$_{0.8}$BKB](NTf$_2$)$_{1.6}$ and maintained at a temperature of 180° C. In order to complete the bond, the cemented crowns were loaded with 20 N at 180° C. for 3 min and then cooled to room temperature for at least 10 min with the load being maintained. The peeling forces were measured at the earliest 1 h after sample preparation. A peeling force of 33.0±8.7 N was measured.

By heating the cemented crowns to 180° C., they were able to be removed from the stumps without force.

Example 6A

Optical Bonding of Transparent Substrates with [Zn$_{0.8}$BKB](NTf$_2$)$_{1.6}$ from Example 4

[Zn$_{0.8}$BKB](NTf$_2$)$_{1.6}$ from Example 4 was processed to form an approx. 90 μm thin film which was placed on a surface of approx. 10×10 mm between two quartz glasses. The site to be bonded was irradiated with light from a point light source (Dr. Hoenle, wavelength range λ=320-390 nm; intensity 900 mW cm$^{-1}$) with pulses of 5×60 s. A good adhesion between the two substrates was achieved. The peeling forces were measured in a universal tensile testing machine (Zwick-Roell Z010). A peeling force of over 1 MPa was measured.

Figure 4:
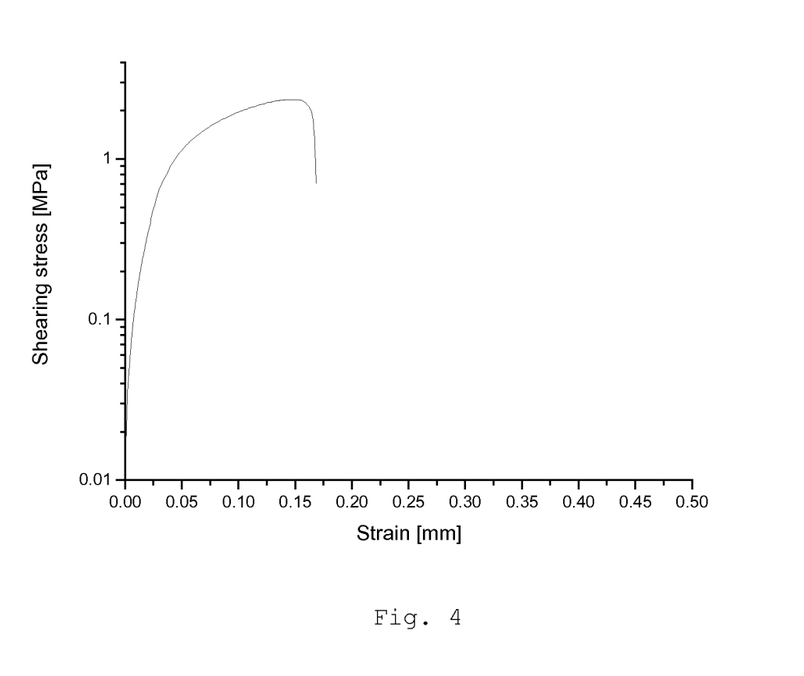

FIG. 4 shows the result of the tensile test on the adhesive bond from Example 6A.

Example 6B

Optical Debonding of an Adhesive Bond of Transparent Substrates with [Zn$_{0.8}$BKB](NTf$_2$)$_{1.6}$ from Example 4

[Zn$_{0.8}$BKB](NTf$_2$)$_{1.6}$ from Example 4 was processed to form an approx. 90 μm thin film which was placed on a surface of approx. 10×10 mm between two quartz glasses. The site to be bonded was heated by means of a heat gun until an air bubble-free bond formed. A good adhesion between the two substrates was achieved.

The sample was then clamped in a universal tensile testing machine (Zwick-Roell 2010) and tensioned such that a force of approximately 53 N acted on the adhesive joint. The adhesive joint was irradiated with UV light from a point light source (Dr. Hoenle, wavelength range λ=320-390 nm; intensity 900 mW cm$^{-1}$). The adhesive bond was debonded after only approximately 30 s.

The invention claimed is:

1. Dental restorative material which comprises a thermolabile polymerizable compound of Formula II:

Formula II, in which

T represents a thermolabile group,

Z$^1$ and Z$^2$ in each case independently represent a polymerizable group selected from vinyl groups, CH$_2$=CR$^1$—CO—O— and CH$_2$=CR$^1$—CO—NR$^2$- or an acid group selected from —O—PO(OH)$_2$, —PO(OH)$_2$ and —SO$_2$OH, wherein at least one Z$^1$ or Z$^2$ is a polymerizable group and at least one Z$^1$ or Z$^2$ is an acid group, Q$^1$ in each case independently is missing or represents an (m+1)-valent linear or branched aliphatic C$^1$-C$_{10}$ radical which can be interrupted by —O—, —S—, —CO—O—, —O—CO—, —CO—NR$^3$- or —NR$^3$—CO—, Q$^2$ in each case independently is missing or represents an (n+1)-valent linear or branched aliphatic C$_1$-C$_{10}$ radical which can be interrupted by —O—, —S—, —CO—O—, —O—CO—, —CO—NR$^3$- or —NR$^3$—CO—, X and Y in each case independently are missing or represent —O—, —S—, —CO—O—, —O—CO—, —CO—NR$^3$- or —NR$^3$—CO—, R$^1$, R$^2$ and R$^3$ in each case independently represent H or a C$_1$-C$_7$ alkyl radical and k, l, m and n in each case independently are 1, 2 or 3.

2. Dental restorative material according to claim 1, in which the thermolabile unit T is a thermolabile group and has the formula -T$^1$••T$^2$-, in which T$^1$ and T$^2$ represent complementary groups which are connected to each other by thermolabile non-covalent interactions.

3. Dental restorative material according to claim 1 in which the thermolabile unit T is an oligomeric or polymeric unit which contains at least one thermolabile group and at least one oligomeric, homopolymeric or heteropolymeric chain P.

4. Dental restorative material according to claim 3, in which the chain P is selected from the group consisting of vinyl, diene, polycondensation and polyaddition oligomers and polymers, copolymers and mixtures thereof.

5. Dental restorative material according to claim 3, in which the chain P has a number average molar mass of from 200 to 20000 g/mol.

6. Dental restorative material according to claim 3, in which the thermolabile unit T has the Formula III or IV:

Formula III,

Formula IV, in which
P in each case independently represents an oligomeric, homopolymeric or heteropolymeric chain which preferably has a number average molar mass of from 200 to 20000 g/mol,
$T^1$ and $T^2$ represent groups which are connected to each other by thermolabile non-covalent interactions,
Q in each case independently is missing or represents a divalent linear, branched and/or cyclic $C_1$-$C_{20}$ radical which can be fully or partly unsaturated and/or aromatic and can be interrupted by —O—, —S—, —CO—O—, —O—CO—, —CO—$NR^3$—, —$NR^3$—CO—, —O—CO—$NR^3$—, —$NR^3$—CO—O— or —$NR^3$—CO—$NR^3$—,
$X^1$ and $X^2$ in each case independently are missing or represent —O—, —S—, —CO—O—, —O—CO—, —CO—$NR^3$—, —$NR^3$—CO—, —O—CO—$NR^3$—, —$NR^3$—CO—O— or —$NR^3$—CO—$NR^3$—,
$Y^1$ and $Y^2$ in each case independently are missing or represent —O—, —S—, —CO—O—, —O—CO—, —CO—$NR^3$—, —$NR^3$—CO—, —O—CO—$NR^3$—, —$NR^3$—CO—O— or —$NR^3$—CO—$NR^3$—,
p in each case independently is 1 to 100 and
q in each case independently is 1, 2, 3 or 4.

7. Dental restorative material according to claim 1, in which the thermolabile group is selected from the group consisting of:

wherein:
$R^4$ is H or a $C_1$-$C_{10}$ alkyl radical,
M is a transition metal or lanthanoid.

8. Dental restorative material according to claim 1, which comprises one or more radically polymerizable monomers.

9. Dental restorative material according to claim 8, which comprises
methyl, ethyl, hydroxyethyl, butyl, benzyl, tetrahydrofurfuryl or isobornyl (meth) acrylate, bisphenol-A-di(meth)acrylate, bis-GMA, UDMA, di-, tri- or tetraethylene glycol di(meth)acrylate, trimethylolpropane tri(meth)acrylate, pentaerythritol tetra-(meth)acrylate, glycerol di(meth)acrylate, 1,4-butanediol di-(meth)acrylate, 1,10-decanediol di(meth)acrylate, 1,12-dodecane-diol di(meth)acrylate,
and/or
one or more N-mono- or disubstituted acrylamides, N-ethyl-acrylamide, N,N-dimethacrylamide, N-(2-hydroxyethyl)acrylamide, N-methyl-N-(2-hydroxyethyl) acrylamide, one or more N-mono-substituted methacrylamides, N-ethylmethacrylamide, N-(2-hydroxyethyl) methacrylamide, N-vinylpyrrolidone, one or more cross-linking allyl ethers,
and/or
one or more cross-linking pyrrolidones, 1,6-bis(3-vinyl-2-pyrrolidonyl)-hexane, one or more cross-linking bisacryl-amides, methylene or ethylene bisacrylamide, one or more cross-linking bis(meth)acrylamides, N,NT-diethyl-1,3-bis(acrylamido)-propane, 1,3-bis(methacrylamido)-propane, 1,4-bis(acrylamido)-butane, 1,4-bis(acryloyl)-piperazine,
and/or
one or more thermolabile cross-linking monomers
or a mixture thereof.

10. Dental restorative material according to claim 1, which comprises one or more radically polymerizable, acid-group-containing monomers.

11. Dental restorative material according to claim 10, which comprises maleic acid, acrylic acid, methacrylic acid, 2-(hydroxymethyl)-acrylic acid, 4-(meth)acryloyloxyethyltrimellitic anhydride, 10-methacryloyloxydecylmalonic acid, N-(2-hydroxy-3-methacryl-oyloxypropyl)-N-phenylglycine, 4-vinylbenzoic acid,
and/or
vinylphosphonic acid, 4-vinylphenylphosphonic acid, 4-vinyl-benzylphosphonic acid, 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid, 2-[4-(dihydroxyphosphoryl)-2-oxa-butyl]-acrylic acid ethyl- or -2,4,6-trimethylphenyl ester
and/or
2-methacryloyloxypropyl mono- or dihydrogen phosphate, 2-meth-acryloyloxyethylphenyl hydrogen phosphate, dipentaerythritol-pentamethacryloyloxyphosphate, 10-methacryloyloxydecyl dihydrogen phosphate, phosphoric acid mono-(1-acryloyl-piperidin-4-yl)-ester, 6-(methacrylamido)hexyl dihydrogen phosphate, 1,3-bis-(N-acryloyl-N-propyl-amino)-propan-2-yl-dihydrogen phosphate, and/or vinylsulphonic acid, 4-vinylphenylsulphonic acid, 3-(methacryl-amido)propylsulphonic acid, or a mixture thereof.

12. Dental restorative material according to claim 1, which comprises an initiator for radical polymerization.

13. Dental restorative material according to claim 1, which comprises a thermally gas-releasing additive.

14. Dental restorative material according to claim 1, which comprises an additive which can convert radiated electromagnetic radiation into heat.

15. Dental restorative material according to claim 1, which comprises organic and/or inorganic filler.

16. Dental restorative material according to claim 1, which comprises
a) 0.1 to 50 wt.-% compound of Formula I,
b) 0.01 to 10 wt.-% initiator,
c) 0 to 80 wt.-% comonomer,
d) 0 to 30 wt.-% adhesive monomer,
e) 0 to 80 wt.-% filler,
f) 0 to 70 wt.-% solvent.

17. Dental restorative material according to claim 15 for use as adhesive, which comprises 0 to 20 wt.-% filler.

18. Dental restorative material according to claim 15 for use as composite, which comprises 20 to 80 wt.-% filler.

19. Method of using a compound comprising a thermolabile compound of Formula I:

$[(Z^1)_m\text{-}Q^1\text{-}X)]_k\text{-}T\text{-}[Y\text{-}Q^2\text{-}(Z^2)_n]_l$   Formula I, in which T represents a thermolabile unit which contains at least one thermolabile group based on non-covalent interactions, $Z^1$ and $Z^2$ in each case independently represent a polymerizable group selected from vinyl groups, $CH_2{=}CR^1{-}CO{-}O{-}$ and $CH_2{=}CR^1{-}CO{-}NR^2{-}$ or an adhesive group selected from $-Si(OR)_3$, $-COOH$, $-O-PO(OH)_2$, $-PO(OH)_2$, $-SO_2OH$ and $-SH$, $Q^1$ in each case independently is missing or represents an (m+1)-valent linear or branched aliphatic $C_1\text{-}C_{20}$ radical which can be interrupted by $-O-$, $-S-$, $-CO-O-$, $-O-CO-$, $-CO-NR^3-$, $-NR^3-CO-$, $-O-CO-NR^3-$, $-NR^3-CO-O-$ or $-NR^3-CO-NR^3-$, $Q^2$ in each case independently is missing or represents an (n+1)-valent linear or branched aliphatic $C_1\text{-}C_{20}$ radical which can be interrupted by $-O-$, $-S-$, $-CO-O-$, $-O-CO-$, $-CO-NR^3-$, $-NR^3-CO-$, $-O-CO-NR^3-$, $-NR^3-CO-O-$ or $-NR^3-CO-NR^3-$, X and Y in each case independently are missing or represent $-O-$, $-S-$, $-CO-O-$, $-O-CO-$, $-CO-NR^3-$ or $-NR^3-CO-$, R, $R^1$, $R^2$ and $R^3$ in each case independently represent H or a $C_1\text{-}C_7$ alkyl radical and k and l in each case independently are 0, 1, 2 or 3 and m and n in each case independently are 1, 2 or 3, as dental restorative material or for the preparation of a dental restorative material.

20. Method of using a compound of Formula I according to claim 19 as adhesive or cement or for the preparation of an adhesive or cement.

21. Method of using a compound of Formula I as defined in claim 19, as reversible adhesive or self-healing plastic material or for producing a reversible adhesive or self-healing plastic material.

22. Method of using of a compound of composition as defined in claim 8, as dental restorative material or for the preparation of a dental restorative material.

23. Method of using a composition as defined in claim 8, as reversible adhesive or self-healing plastic material or for producing a reversible adhesive or self-healing plastic material.

24. Dental restorative material according to claim 1, which comprises
a) 1 to 40 wt.-% compound of Formula II,
b) 0.1 to 3.0 wt.-% initiator,
c) 1 to 60 wt.-% comonomer,
d) 0.5 to 15 wt.-% adhesive monomer,
e) 0 to 80 wt.-% filler,
f) 0 to 70 wt.-% solvent.

25. Dental restorative material according to claim 1, which comprises
a) 2 to 30 wt.-% compound of Formula II,
b) 0.2 to 2 wt.-% initiator,
c) 5 to 50 wt.-% comonomer,
d) 1 to 5 wt.-% adhesive monomer,
e) 0 to 80 wt.-% filler,
f) 0 to 70 wt.-% solvent.

26. Dental restorative material according to claim 1, which comprises
a) 5 to 30 wt.-% compound of Formula II,
b) 0.01 to 10 wt.-% initiator,
c) 0 to 80 wt.-% comonomer,
d) 0 to 30 wt.-% adhesive monomer,
e) 0 to 80 wt.-% filler,
f) 0 to 70 wt.-% solvent.

* * * * *